US009801699B2

(12) United States Patent
Okay

(10) Patent No.: US 9,801,699 B2
(45) Date of Patent: Oct. 31, 2017

(54) PAIRED TEMPLATES FOR PLACING DENTAL IMPLANTS AND ENHANCING REGISTRATION FOR DENTURE PROSTHETICS ATTACHED TO THE IMPLANTS

(71) Applicant: Devin Okay, New York, NY (US)

(72) Inventor: Devin Okay, New York, NY (US)

( * ) Notice: Subject to any disclaimer, the term of this patent is extended or adjusted under 35 U.S.C. 154(b) by 831 days.

(21) Appl. No.: 14/048,872

(22) Filed: Oct. 8, 2013

(65) Prior Publication Data

US 2014/0272779 A1 Sep. 18, 2014

Related U.S. Application Data

(60) Provisional application No. 61/781,766, filed on Mar. 14, 2013.

(51) Int. Cl.
| | |
|---|---|
| *A61C 13/00* | (2006.01) |
| *A61C 8/00* | (2006.01) |
| *A61C 9/00* | (2006.01) |
| *A61C 1/08* | (2006.01) |

(52) U.S. Cl.
CPC .......... *A61C 13/0004* (2013.01); *A61C 1/084* (2013.01); *A61C 8/005* (2013.01); *A61C 8/0089* (2013.01); *A61C 9/0053* (2013.01)

(58) Field of Classification Search
CPC ..... A61C 13/0004; A61C 1/084; A61C 8/005; A61C 8/0089; A61C 9/0053
See application file for complete search history.

(56) References Cited

U.S. PATENT DOCUMENTS

| | | | | |
|---|---|---|---|---|
| 2,233,722 | A | * | 3/1941 | Weigele ................. A61C 19/00 433/76 |
| 4,742,464 | A | | 5/1988 | Duret et al. |
| 5,569,578 | A | | 10/1996 | Mushabac |
| 5,769,633 | A | | 6/1998 | Jacobs et al. |
| 5,890,896 | A | | 4/1999 | Padial |
| 6,788,986 | B1 | | 9/2004 | Traber et al. |
| 7,228,191 | B2 | | 6/2007 | Hofineister et al. |
| 7,474,932 | B2 | | 1/2009 | Geng |
| 7,623,942 | B2 | | 11/2009 | Touchstone |
| 7,774,084 | B2 | | 8/2010 | Cinader, Jr. |
| 7,835,811 | B2 | | 11/2010 | Schmitt |
| 7,887,327 | B2 | | 2/2011 | Marotta |
| 7,909,606 | B2 | | 3/2011 | Marcell |
| 7,909,607 | B2 | | 3/2011 | Yau et al. |

(Continued)

*Primary Examiner* — Cris L Rodriguez
*Assistant Examiner* — Hao D Mai
(74) *Attorney, Agent, or Firm* — Cooper & Dunham LLP

(57) ABSTRACT

A denture is registered and secured to implants with the help of paired surgical-prosthetic implants fabricated based on 3D imaging of the patient's mouth and the denture. The surgical template has guide holes that are located and oriented to guide dental instrumentation forming accurately located and oriented osteotomies for the implants. The prosthetic template conforms to the denture and has guide holes that are located and oriented such that connection holes in the denture can be formed through the guide holes in the paired prosthetic template. The connection holes clear the replacement teeth of the denture and line up with the implants. Attachment elements can be inserted through the connection holes in the denture to secure the denture to the implants.

19 Claims, 5 Drawing Sheets

(56) References Cited

U.S. PATENT DOCUMENTS

| | | |
|---|---|---|
| 8,021,154 B2 | 9/2011 | Holzner et al. |
| 8,083,522 B2 | 12/2011 | Karkar et al. |
| 8,135,492 B2 | 3/2012 | Yau et al. |
| 8,145,340 B2 | 3/2012 | Taub et al. |
| 8,195,320 B2 | 6/2012 | Garcia-Aparicio |
| 8,280,542 B2 | 10/2012 | O'Brien et al. |
| 2006/0093988 A1 | 5/2006 | Swaelens et al. |
| 2008/0020343 A1 | 1/2008 | Mount |
| 2008/0227056 A1* | 9/2008 | Bulard .................. A61C 1/084 433/172 |
| 2009/0011382 A1* | 1/2009 | Bavar .................... A61C 1/084 433/76 |
| 2009/0248184 A1 | 10/2009 | Steingart et al. |
| 2009/0287332 A1 | 11/2009 | Adusumilli et al. |
| 2009/0325127 A1 | 12/2009 | Kusch et al. |
| 2009/0325128 A1 | 12/2009 | Holzner et al. |
| 2010/0105008 A1 | 4/2010 | Powell et al. |
| 2010/0203478 A1 | 8/2010 | Rubbert |
| 2010/0273124 A1 | 10/2010 | Borczyk |
| 2010/0316974 A1 | 12/2010 | Yau et al. |
| 2010/0332248 A1 | 12/2010 | Pettersson |
| 2011/0010187 A1 | 1/2011 | Andersson et al. |
| 2011/0060558 A1 | 3/2011 | Pettersson et al. |
| 2011/0086328 A1 | 4/2011 | Wedeking |
| 2011/0183289 A1 | 7/2011 | Powell et al. |
| 2011/0269104 A1 | 11/2011 | Berckmans, III et al. |
| 2012/0015328 A1 | 1/2012 | Giasson et al. |
| 2012/0070802 A1 | 3/2012 | Woodward, III |
| 2012/0070803 A1 | 3/2012 | Manai et al. |

\* cited by examiner

PAIRED TEMPLATES FOR PLACING DENTAL IMPLANTS AND ENHANCING REGISTRATION FOR DENTURE PROSTHETICS ATTACHED TO THE IMPLANTS

REFERENCE TO RELATED APPLICATIONS

This application claims the benefit of provisional application No. 61/781,766 filed Mar. 14, 2013 and hereby incorporated by reference in this patent specification.

FIELD

This patent specification pertains to fabricating and using two distinct and separate but paired surgical-prosthetic templates for placing implants in a patient jawbone and ensuring good registration between the implants and a denture that they support.

BACKGROUND OF THE TECHNOLOGY

Using implants for dental restoration of completely or partially edentulous patients has become widely accepted practice. In a two-stage restoration, the first stage involves an incision through the gingiva to expose the underlying bone. The dentist uses a series of progressively larger drill bits or burs to form an osteotomy in the jawbone, places a dental implant that typically comprises a titanium cylinder with a leading end threaded on the outside and a trailing end with a threaded bore, seals the bore with a cover screw, and sutures gum tissue over the implant and cover screw. Healing and osteointegration continue for weeks or months, after which the second stage starts. The dentist re-opens gum tissue, removes the cover screw, and secures a healing abutment to the exposed end of the implant to allow gum tissue to heal around the abutment. After healing, the abutment is removed, an impression coping is screwed into the implant, and an impression is taken, from which a prosthesis is made and definitively secured to the implant. An alternative, single-stage procedure involves forming the osteotomy, placing the implant and possibly immediately securing a prosthesis to the implants. In a single-tooth restoration, the prosthesis restores the appearance of the tooth. The prosthesis can also be in the form of a partial denture supported by two or more implants. Or, it can be a denture supported by several implants and possibly replacing all teeth in a dental arch.

In some cases, the dentist uses a surgical template to assist in the process of creating the osteotomy. One way to make the surgical template is to take a CT scan of the patient's mouth and use the resulting three-dimensional (3D) image and computer-aided-design (CAD) software to develop a virtual guide that shows proposed locations and other information regarding the planned implant(s). Computer-aided-manufacturing (CAM) software and equipment can use the virtual template to fabricate the actual surgical template, which the dentist registers or fixates in the patient's mouth to prepare implant osteotomies by drilling through guide holes in the template.

SUMMARY OF THE DISCLOSURE

This patent specification describes products and processes that improve the placement of implants and facilitate accurate registration between the implants (and any remaining natural teeth) and a denture secured to the implants. The implants can be placed and the denture secured to them in a single-stage surgery that is particularly efficacious. The new approach creates two separate but paired CAD-CAM surgical-prosthetic templates, a first or surgical template is used in forming osteotomies for the implants and a second or prosthetic template is used for registering the denture and attaching it to the implants.

The second template has guide holes through which to form connection holes in the denture. The dentist forms the implant osteotomies using the first template, and then places in the patient's mouth the denture that has been modified with connection holes through use of the second template and was worn by the patient during the CT scan and registered through software planning. The second template fits over the denture and, if applicable, any remaining natural teeth. Because of the way the second template is designed and manufactured, its guide holes match up to the position and angulation of the implants. Attachment abutments that are placed through prepared connection holes in the denture are fitted to the denture and secure the denture to the implants with screws. The denture prosthesis then becomes fixed into the implants but can be retrieved by the dentist or surgeon.

Creating the new paired surgical-prosthetic templates involves using a 3D imaging modality such as CT to image the patient's mouth with the denture in place, and using the resulting 3D image or images to form virtual templates that account for where implants should be placed and how they should be oriented relative to the patient's bone structure, soft tissue, and any existing teeth, where they should be relative to the denture structure or proposed tooth replacement, and there the connection holes in the denture should be relative to the implants and the denture structure. These virtual templates also can inform the selection of implants in terms of size and other parameters, the selection of attachments for attaching implants to the denture, and the selection of which drill bits or burs, instrumentation and techniques to use and in what sequence. The paired virtual templates are designed through CAD software that may provide interactive facilities for input by the dentist, surgeon or technician.

The new templates are paired to the virtual placement of the implants and register their position and angulation through the occlusal or palatal surface of the denture. For each implant, a virtual abutment from the implant is registered in the denture with CAD software in the same planning file, and its position and angulation are projected for creating a matching guide hole in the new virtual prosthetic template that is designed over the external denture surfaces, preferably occlusal, palatal and facial surfaces. In one example, each guide hole is at least 5 mm in height and has a standard metal insert assuring its diameter. All guide holes for the denture are recorded in one prosthetic template so that it may fit onto the denture and so that the guide holes can prepare the denture for fixation to the implants.

The virtual templates are used to manufacture the actual paired templates, for example through a CAM process. In one example, after forming the osteotomies using the first actual CAD-CAM template, the implants are placed in the patient's jaw and evaluated for initial stability. For example, the first actual template can be secured to the jaw using existing teeth and/or pins secured to the patient's jawbone. The second template is placed over the denture and is inherently in good registration with the denture and the implants due to the way in which the templates were created. Through guide holes formed in the second template in the process of manufacturing it, and through connection holes in the denture that can be formed with the help of the second template, the dentist installs attachment abutments to secure the denture to the implants. Alternatively, implant osteotomies are formed by drilling, through the guide holes in the surgical CAD-CAM template, into the bone stration and the implants can be placed through the connection holes of the denture which is in position over the tissue bearing surface. Due to using the same design and manufacture plan in planning and manufacturing each of the paired templates, the connection holes in the denture are in good registration with the implants. In one example, the paired surgical and prosthetic templates are manufactured by stereolithography, a laser driven polymerization process, and finished by hand with metal inserts into the desired diameter guide holes. In another example, the templates are fabricated by incorporating CAD-CAM rapid prototyping milling techniques into the process.

It is preferable to use the paired surgical-prosthetic templates in a single-stage surgical-prosthetic procedure to place the implants and attachments to the denture, but an alternative is to use a two-stage procedure to place the implants and allow time for osteointegration or healing. Then, the denture connection holes can be formed by drilling connection holes in the denture through guide holes on the second paired template. Attachment abutments are fitted into those connection holes for fixating the denture to implants.

DETAILED DESCRIPTION OF PREFERRED EXAMPLES

FIGS. 1-5 illustrate an example of using the new, paired surgical-prosthetic template system to place implants in bone and secure the denture to the implants. The figures are illustrative and not to scale. They show one of several possible variations of implants and it should be understood that the disclosed principles apply to the use of implants and attachment hardware from different manufacturers who offer differently shaped components.

Figure 1:
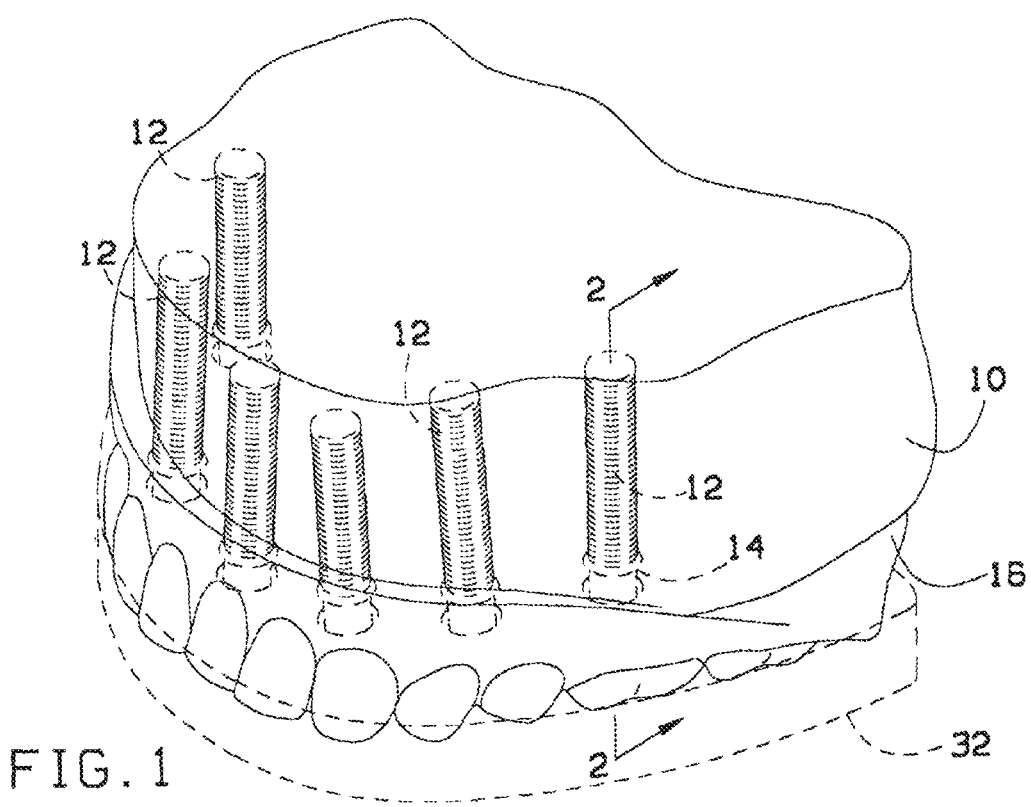
FIG. 1 is a perspective view illustrating implants and attachment abutments extending through connection holes in a denture.
Figure 2:
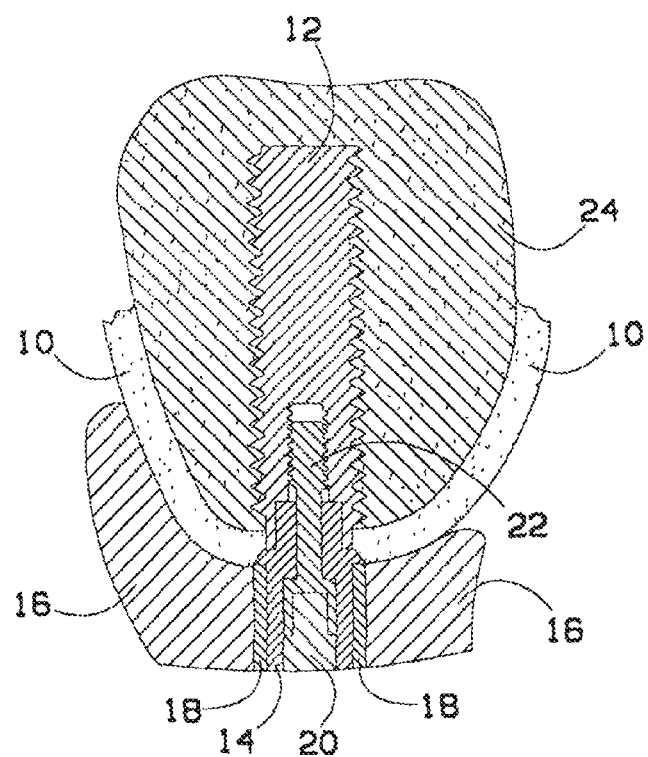
FIG. 2 is a sectional view taken along line 2-2 of FIG. 1.
Figure 3:
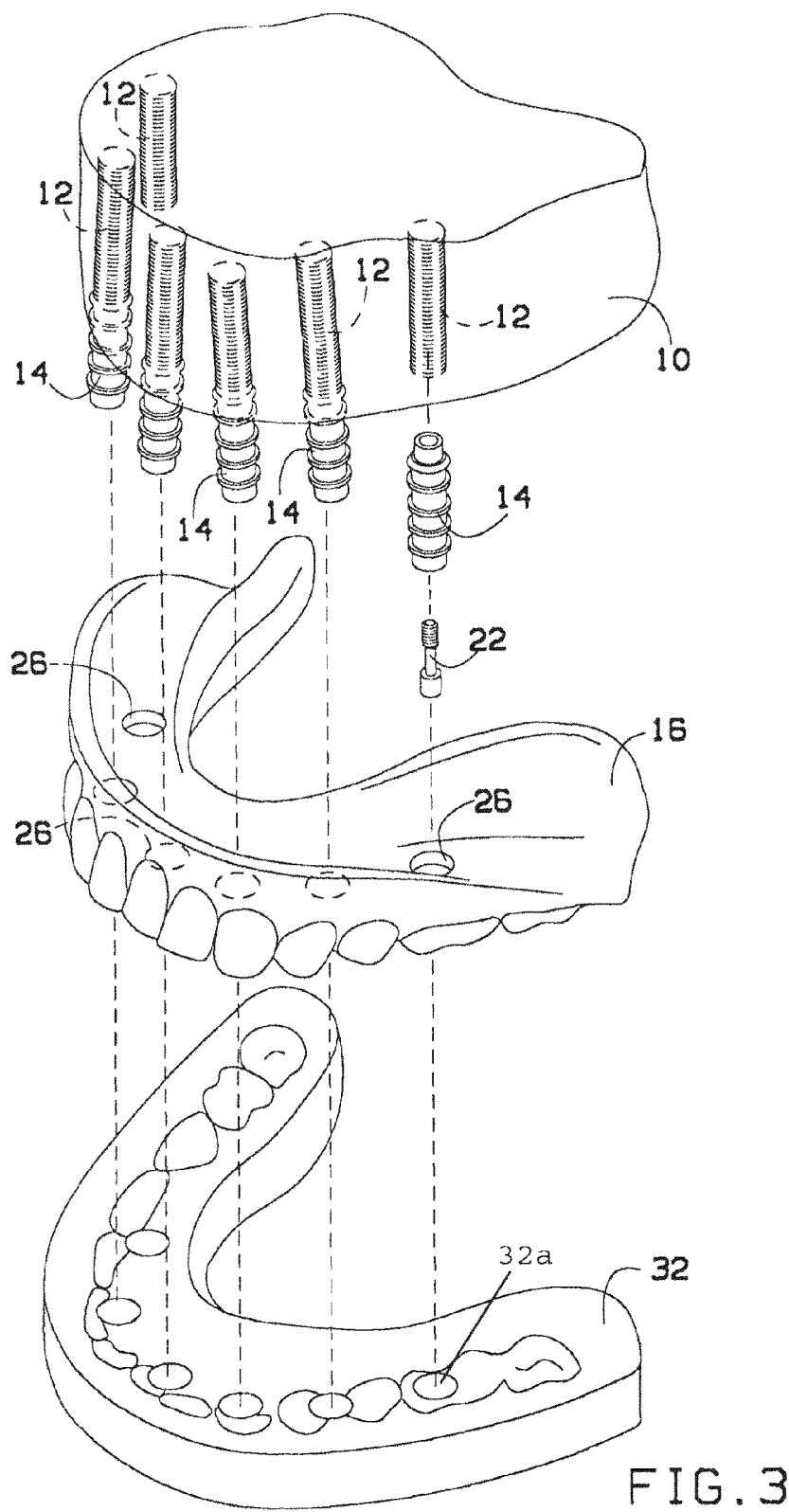
FIG. 3 is an exploded perspective view of FIG. 1.

Each of implants 12 is in bone 24 and is secured to denture 16 by attachments that include cylinders 14 and screws 22 and pass through connection holes 26 (see FIG. 3) in the denture and through gum 10. The attachments are configured through guide holes 32a in a prosthetic template 32 that is paired with a surgical template 29 schematically illustrated in FIG. 4. As seen in FIG. 2, each implant 12 is in bone 24 and is secured to denture 16 by implant abutment cylinder 14 that is held to implant 12 with a screw 22. The free end of cylinder 14, which extends away from bone 24, fits in a connection hole 26 in denture 16 and can be further secured to the denture with light-cured resin 18. Connection holes 26 in denture 16 preferably are larger than the end of cylinders 14 to allow for fine adjustments by varying thickness of resin. As seen in FIG. 1, connection holes 26 are at locations that avoid elements of denture 16 that should not be disturbed or weakened, such as the tooth structure. Resin 18 is a flowable material when placed in the space between cylinder 14 and connection hole 26 to allow such adjustment once it is light-cured later. The opening in the free end of cylinder 14 can be filled in with material that can be removed when access to screw 22 is needed.

Creating the paired prosthetic template 32 involves first making a denture, for example by using a traditional technique to take a mold of the patient's mouth that is sent to a dental laboratory to fabricate a denture configured for a completely or partially edentulous patient. Alternatively, more recent technology can be used to rely on other ways to record the necessary shape information, for example using laser measurements. The denture can be fabricated using casting processes or using CAM technology. The dentist may elect to make fine adjustments when fitting the denture and testing occlusion. In addition, patient acceptance of their appearance, tooth display and overall esthetics can be confirmed prior to implant surgery and immediate restoration.

After the denture is finalized, the patient's mouth is imaged with the denture in place, using a three-dimensional (3D) imaging modality such as CT, to generate one or more 3D images of the patient's mouth and of the denture. In addition, denture 16 alone can be similarly CT scanned to generate one or more 3D images of the denture alone. The 3D images can take different forms depending on the imaging and image reconstruction software that the dentist selects, as different types of software are currently available from different manufacturers and other software may become available in the future.

The dentist can visualize the 3D images, in sectional or perspective views on a computer screen, and can interactively develop a surgical plan. One example of such software is Nobel Clinician Software available from Nobel Biocare, Yorba Linda, Calif., and another example is SimPlant from CSI-Materialise, Leuven, Belgium. Both have been used to design conventional surgical templates (but not the paired surgical-prosthetic templates described in this patent specification and their use to register and connect implants to a denture). A surgical plan that involves the denture can be made using the same software according to the teachings of this patent specification, because the 3D image already includes an image of the denture when taken according to this patent specification. An enhancement of such software to include a separable image of the denture can be made according to the teachings of this patent specification without undue experimentation by a person skilled in the technology. Or, a separate 3D image of the denture can be made with a separate scan of the denture alone and then scaled and integrated with a 3D image of the patient's mouth. There can be fiduciary markers or radio-opaque material incorporated into the denture to relate the two scans.

The 3D image of the patient's mouth with the denture in place is converted to an image of a 3D virtual model that defines: (a) virtual implant placement 28 in bone 24 (FIG. 4) that conforms to selected rules regarding bone dimensions and locations of implants for supporting denture 16; (b) a virtual surgical template 29 (FIG. 4) that, when converted to an actual surgical template, facilitates accurate implant placement; (c) a virtual prosthetic template 32 (FIGS. 3 and 4) with guide holes 32a that is paired with the virtual surgical template and thus with implant placement and, when converted to an actual prosthetic template, facilitates attaching denture 16 to implants 12, and (d) a virtual denture 16 (FIG. 3) with connection holes 26 for attachment to the implants.

The virtual implant placement can contain information regarding the location, orientation, diameter and depth of osteotomies, the size of implants, and other parameters. It conforms to rules regarding bone characteristics, number and locations and orientation of implants needed to support the denture, and other parameters that are known in implant placement practice and technology. The virtual model of surgical template 29 reflects the application of these rules for implant placement. The placement of connection holes 26 in the virtual denture 16 also conforms to applicable rules, in addition to matching the geometric projections of the implants onto the denture. Those rules include ensuring that connection holes 26 in denture 16 do not disturb or weaken denture elements such as teeth. The virtual prosthetic template 32 also conforms to rules that ensure that guide holes 32a match the implants in location and orientation and also take into account other parameters such as ensuring that the axial length of guide holes 32a would provide sufficient support for drill bits or burs. Guide holes 32a can be lined with metal guiding cylinders 34 (FIG. 5) to help orient drill bits or burs and to provide durability. Different sizes metal guiding cylinders can be used at different times in this procedure, to match different diameter drill bits or burs that can be used in different stages of the drilling process and to match different sizes of implant abutment cylinders.

Figure 4:
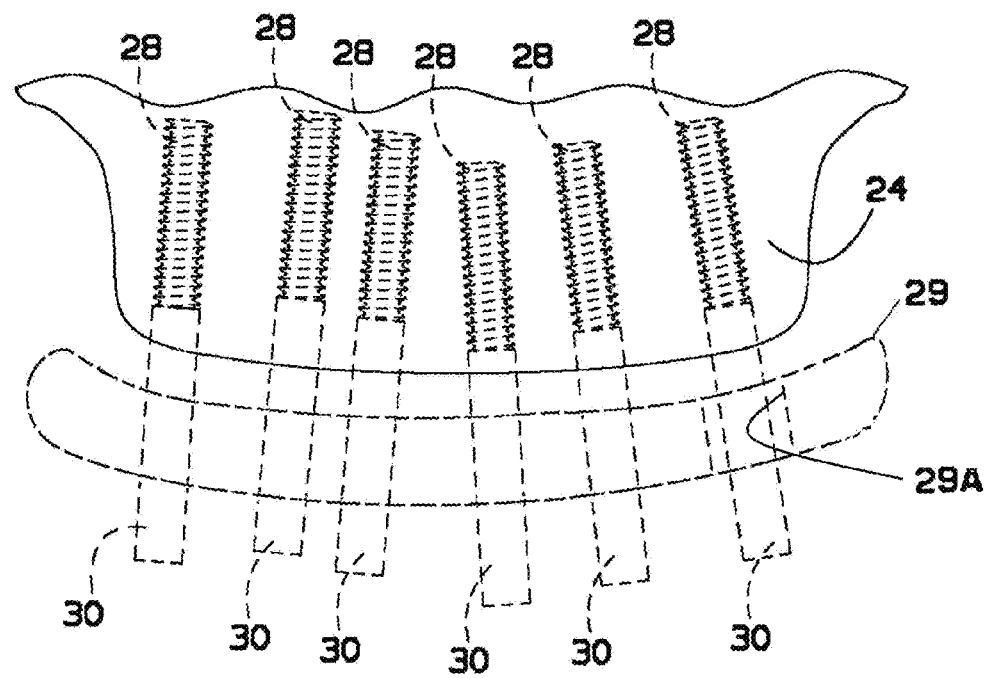
FIG. 4 illustrates virtual implant placement, a virtual paired surgical template, and virtual abutments.

FIG. 4 illustrates a stage of developing the virtual implant placement and paired surgical template 29. It represents a screen view showing patient's bone 24 and locations and orientations of implants positions 28 in plan front view, as well as locations of possible abutments 30. It also shows in schematic form a surgical template 29 with guide holes 29a to guide the placement and orientation of drill bits or burs when forming osteotomies for implant placement. As in known in implant practice, the diameters of guide holes 29a can be different for different stages of osteotomy formation, which can be achieved by making several surgical templates that differ in the diameters of the guide holes or by using different sleeves in guide holes 29a at different times. The view in FIG. 4 is an example of several different views that are available; other views such as perspective and sectional views also are available from currently available planning software and typically are viewed by the dentist or surgeon in considering and adjusting the virtual implant placement and the virtual surgical template.

Figure 5:
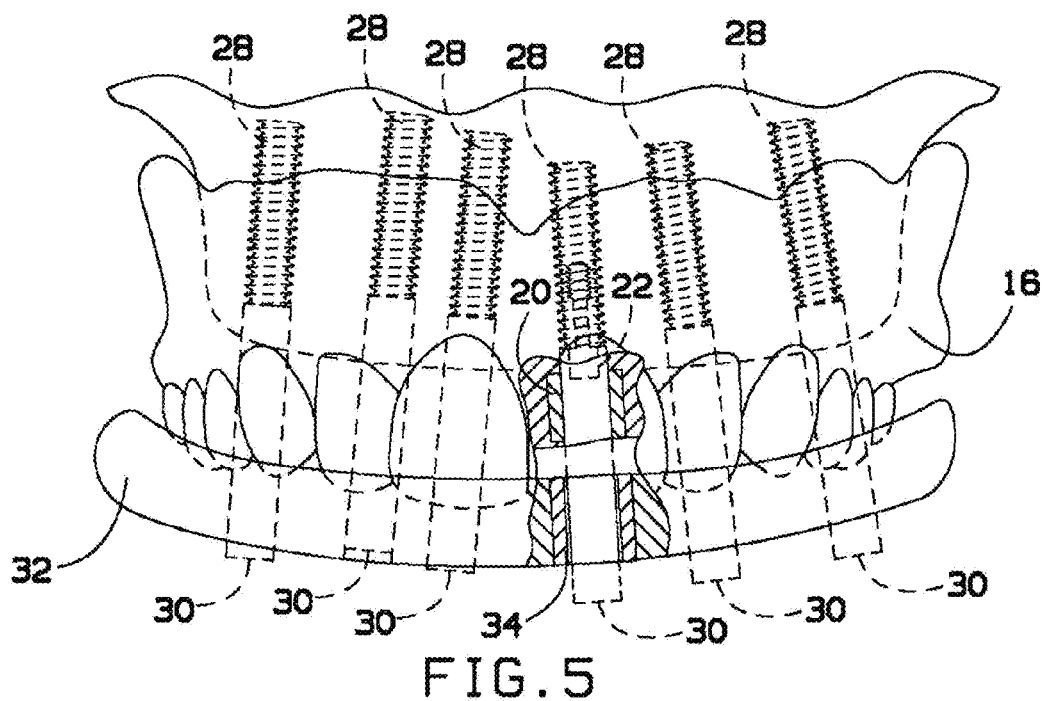
FIG. 5 is a front elevation illustrating use of the CAD-CAM paired prosthetic template over a denture and also illustrating how the location and angulation of its guide holes are indexed through the occlusal or palatal surfaces.

FIG. 5 illustrates a front elevation of the patient's mouth, with denture 16 and paired prosthetic template 32 in place. The same figure also can be considered as a view of the virtual prosthetic template that can be adjusted in the course of constructing the surgical plan. Abutments 30 can be used in the course of the procedure for temporary alignment of denture 16 and prosthetic template 32 with implants 28, as abutments 30 are temporarily affixed to the implants at locations 28 and pass through connection holes 26 in denture 16 and guide abutment cylinders 34 in guide holes 32a of paired prosthetic template 32. FIG. 5 also can be considered as illustrative of a screen view available to the dentist in creating the surgical plan, to help visualize the illustrated items and their relationship. Many other views also are available to the dentist in constructing the surgical plan, such as sectional views, plan views, etc., as known in the implant modeling technology.

After the virtual implant placement, virtual surgical template, virtual prosthetic template with the actual denture image are finalized through the process described above, the resulting digital file is used to fabricate the actual paired surgical template 29 and prosthetic template 32. For example, the digital file can be an input to a CAM process that fabricates the actual paired surgical and prosthetic templates. This fabrication can use stereolithography available from SurgiGuide, CSI Materialise, Glen Burnie, Md., or 3D printing available from i-dent Imaging, Fort Lauderdale, Fla., or some other known or future process that produces an actual 3D item from a digital file that defines it.

The dentist or a dental laboratory can use the actual prosthetic template 32 to line its guide holes 32a with suitable metal cylinders 34 and to drill through them connection holes 26 in denture 16. Subsequently, the dentist can install the denture 16 in the patient's mouth and secure it to the implants. After forming osteotomies and placing implants 12 at locations 28, the dentist can attach denture 16 by inserting plastic implant cylinders 14 and screws 22 through guide holes 32a in paired prosthetic template 32 and through connection holes 26 in denture 16, injecting and curing resin 18, and filling in retrievable material 20. Alternatively, other known attachments can be used to attach denture 16 to implants 28 permanently or removably (e.g., with overdenture attachments). The formulation of light cure polymer resins may include tooth colored or pink radio-opaque or radiolucent materials.

Figure 6A:
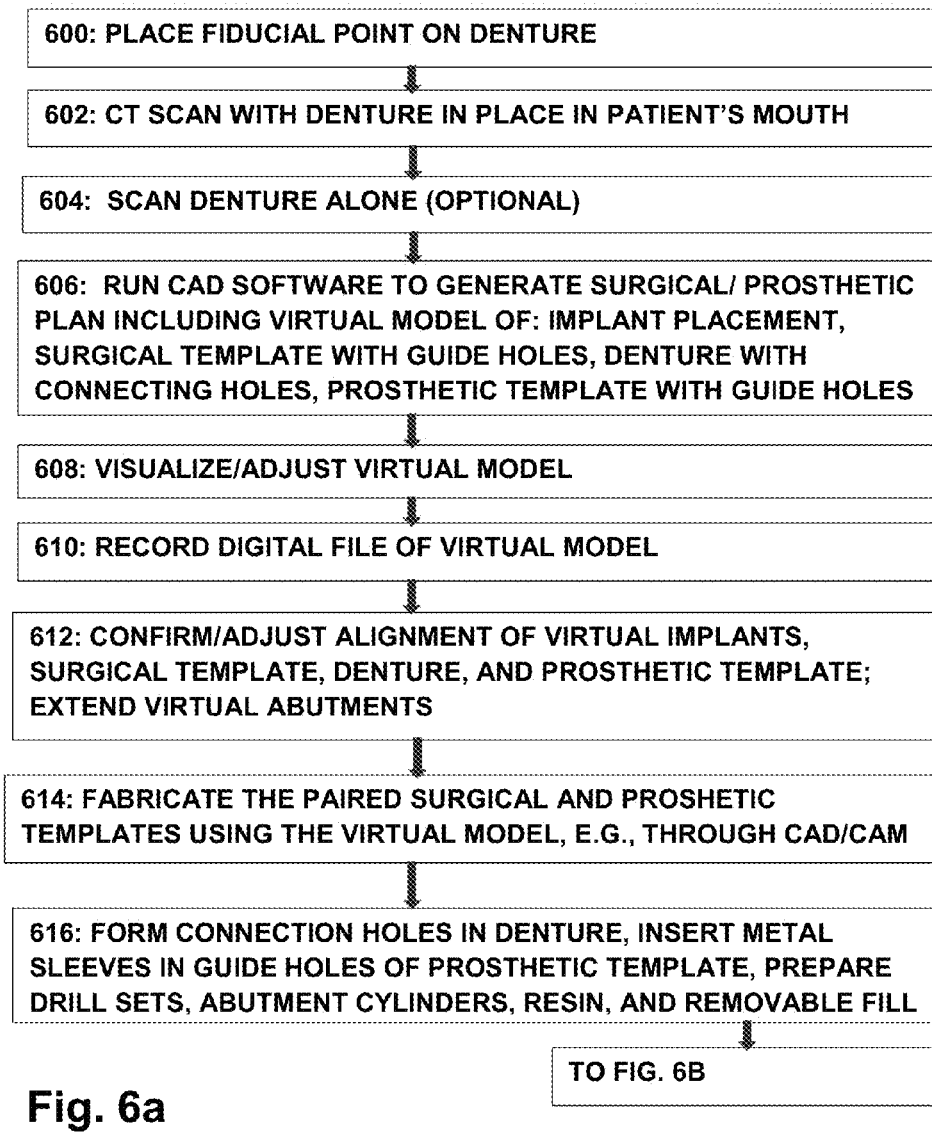
FIGS. 6a and 6b are a functional diagram of an example of creating and using paired surgical-prosthetic templates.
Figure 6B:
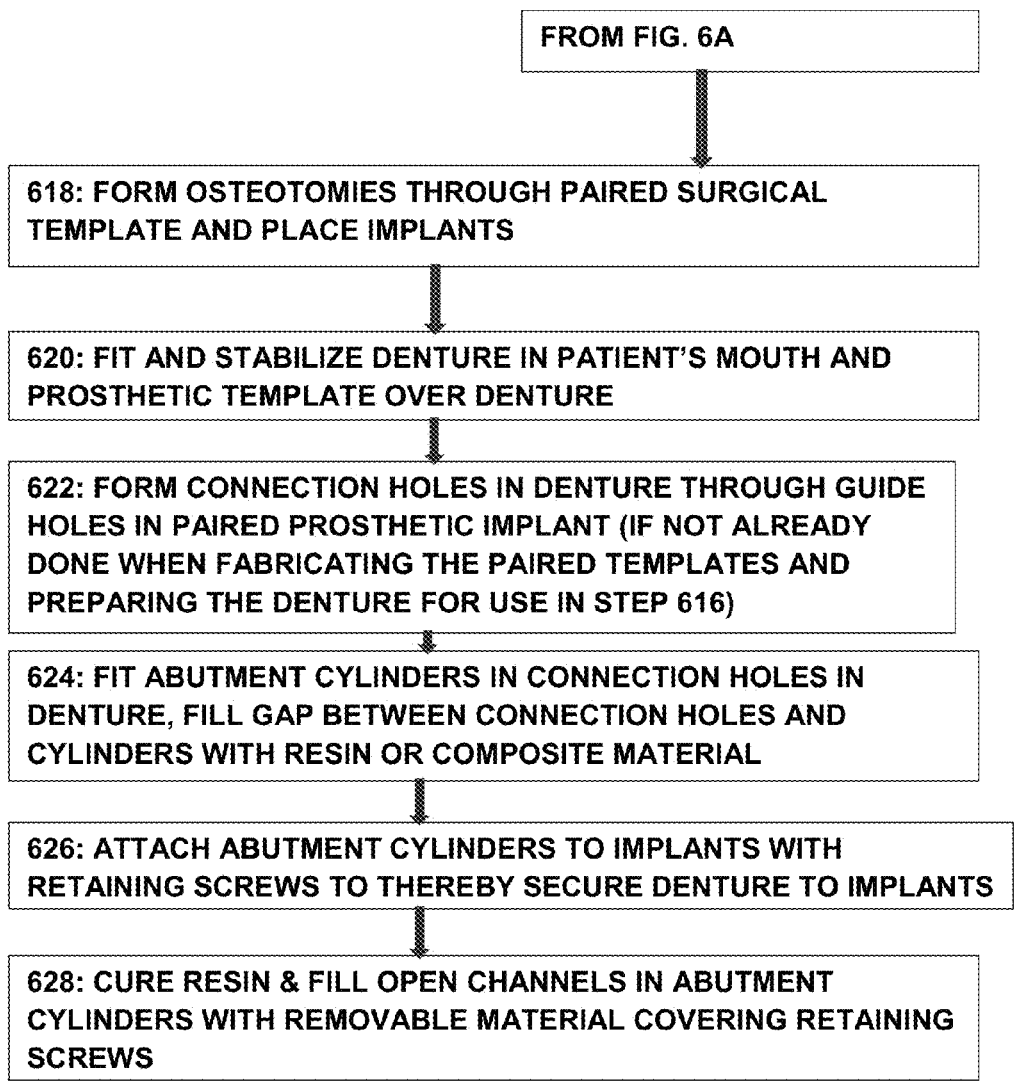

Major steps of an example using the new type of paired surgical-prosthetic templates are illustrated in FIGS. 6a and 6b. Some of the steps are optional. An assumption is made that the process starts after confirmation that the patient's bone structure in the mouth is sufficient to support the implants and the denture, perhaps after suitable bone implant procedures.

In FIG. 6a, step 600 includes adding fiducial markers to denture 16 that stand out in the 3D image of the denture because of difference in x-ray attenuation or other properties. Existing distinctive features of denture 16 can serve as fiducial markers in some cases. The denture is fabricated or processed with rigid materials without undesirable backscatter when scanned. In one method, the fiduciary markers can be made with tooth colored and pink radio-opaque light cured polymer resin. In another method, a framework can be incorporated into the restoration with CAD-CAM or more conventional techniques.

In steps 602, a 3D modality such as CT scans the patient's mouth with denture 16 in place. In optional step 604, an additional scan of the denture alone may be taken, and the resulting 3D image of the denture can be changed in size and orientation to match the denture as seen in the image of the patient's mouth with the denture in place.

In steps 606, the 3D image data that define the pertinent patient anatomy and the denture are processed using software of the type discussed above (for example as available from Nobel Biocare) to develop a surgical plan that includes a virtual image of the jawbone and the planned implant locations, a virtual image of a surgical template with guide holes matching the implants in location and orientation, a virtual image of the denture with connection holes that line up with the implants in location and orientation, and a virtual image of a prosthetic template with guide holes that line up with the connection holes in the denture and the implants in location and orientation. In optional step 608, denture 16 can be visualized alone, to further help the dentist formulate the surgical plan and to assess possible positions of the connection holes in the denture. In step 610 the computer running the software records the positions and angulations of the planned implants, conforming to selected rules that take into account the topography of denture 16 in addition to bone and other parameters.

In step 612, planning software that created the virtual modes displays selected views of the model to the dentist and the dentist makes adjustments in the virtual model, for example through interface devices such as a track pad, a track ball or a mouse, or through a touch screen, to thereby change parameters such as location and angulation of implants, and in guide and connection holes and to ultimately confirm the virtual model of the implant location and orientation, the surgical template and its guide holes, the denture and its connection holes, and the prosthetic template and its guide holes. In this step, the planning software may also extend a virtual image of abutments 30 through the connection holes in the denture for visualization by the dentist.

In step 614, CAD-CAM software and equipment of the type described above fabricate surgical template 29 and prosthetic template 32. The two templates are paired in that the guide holes in each are aligned with each other and with the intended implant placement and connection holes defined in the virtual model of the denture.

In step 616, the dentist of the dental office staff or laboratory form connection holes in the denture, for example by mating denture 16 with prosthetic template 32 and drilling through guide holes 32*a* in prosthetic template 32, which have previously placed metal guide cylinders 34 in guide holes 32*a*. Additional procedures that can be carried out as a part of this step include selection and preparation of a set of drill bits or burs for drilling connection holes 26 in denture 16, and plastic or other material abutment cylinders 14 for connecting implants 28 to denture 16 (FIG. 2) with abutment screws 22, and of resin 18 (FIG. 2) or other materials to secure cylinders 14 to denture 16, and filling material 20 (FIG. 2).

The steps illustrated in FIG. 6*b* follow, in which the dentist uses the templates and other elements prepared in the steps of FIG. 6*a* to place the implants and secure the denture to the implants.

In step 618, the dentist places the surgical template 29 in the patient's mouth in registration with bone 24 and forms osteotomies at the locations and in the orientations matching those of the virtual model, by drilling through guide holes 29*a*, typically with successively greater diameter drills of burs.

In step 620, the dentist replaces surgical template 29 with denture 16, fits prosthetic template 32 over the denture, and stabilizes the denture and the prosthetic template in registration relative to each other and to the patient's jawbone as in the virtual model confirmed in step 612.

In step 622, if connection holes 26 had not been formed in denture 16 in step 616, the dentist drills those holes in denture 16 through guide holes 32*a*. Because of the way paired templates 29 and 32 and connection holes 26 in denture 16 were designed and fabricated, and the way the templates and the denture were fitted and registered in the patient's mouth, implants 12, connection holes 26 and guide holes 32 are axially aligned and in good registration at this stage of the process.

In step 624, the dentist fits abutment cylinders 14 into the connection holes 26 of denture 16, and fills the space between the cylinders and the connection holes with a flowable resin 18 or other suitable luting material. This allows for final adjustment because it permits some deviation between the axes of implants 12 and the axes of the respective connection holes 26.

In step 626, the dentist attaches abutment cylinders 15 to implants 12 with attachment screws 22 to thereby secure denture 16 to implants 12. This action may result in some portions of the periphery of abutment cylinders 14 to be closer to the inner walls of connection holes than other portions, but the flowable nature of resin 18 or similar material causes it to fill all the space between the abutment cylinders 14 and holes 26.

In step 628, the dentist cures resin 18, for example with visible light to initiate polymerization, or otherwise solidifies material 18 to form solid material in the space between cylinders 14 and holes 26, and fills the remaining opening in cylinders 14 with material that is solid or solidifies but can be removed by the dentist if access to screws 22 is needed at a future time. This fixes denture 16 to implants 12. If a removable attachment is preferred, different attachment hardware can be used in place of cylinders 14 and screws 22 as in known in the pertinent technology.

While several embodiments are described, it should be understood that the new subject matter described in this patent specification is not limited to any one embodiment or combination of embodiments described herein, but instead encompasses numerous alternatives, modifications, and equivalents. In addition, while numerous specific details are set forth in the following description in order to provide a thorough understanding, some embodiments can be practiced without some or all of these details. Moreover, for the purpose of clarity, certain technical material that is known in the related art has not been described in detail in order to avoid unnecessarily obscuring the new subject matter described herein. It should be clear that individual features of one or several of the specific embodiments described herein can be used in combination with features or other described embodiments. Further, like reference numbers and designations in the various drawings indicate like elements.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims. This includes the use of paired template systems for the registration of denture prosthetics with frameworks for fixed and removable restorations, definitive or interim restorations. In one method, the modified denture with the connection holes prepared from the prosthetic template represents a pattern and has all surfaces digitally scanned, registered and confirmed and is used to fabricate a CAD-CAM restoration with a framework made of ceramic and/or zirconium or titanium for a definitive restoration using prototype methodology such as milling techniques, with or without sintering for ceramic materials. The restoration is attached to the implants as previously described with a compatible abutment cylinder. In addition, the denture can be represented by 3D image data in the process of creating the virtual model, and an actual denture can be fabricated by CAM or other equipment from that virtual model. The virtual model of the denture can be generated by scanning an actual denture, or it can be generated by scanning the patient's mouth and adjusting the resulting 3D image as needed in an interactive process with input from a dentist or other professionals. The system and method disclosed above include computer programs to control the creation of the virtual model and the fabrication of actual paired templates and dentures.

Any patents or other publications, including patent applications identified above, are hereby incorporated by reference in this patent specification as though fully set out herein.

The invention claimed is:

1. A method of placing implants in a patient's jawbone and securing a denture thereto, comprising:
   providing a denture configured for a completely or partially edentulous patient;
   imaging the patient's mouth and the denture with a three-dimensional (3D) imaging modality to generate a 3D image of the patient's jawbone and of the denture;
   processing the 3D image with a computer configured to generate a 3D virtual model of:
   a. implant placement that conforms to selected rules regarding bone dimensions and implant location for supporting the denture;
   b. a paired surgical implant template configured for the implant placement;
   c. a paired prosthetic template conforming to an occlusal side of the denture and having guide holes that conform to the implant placement and to the denture; and
   d. the denture and connection holes through the denture that conform both to the implant placement and to selected rules regarding clearance from denture elements;
   fabricating an actual surgical template based on said 3D virtual model of the paired surgical implant template and a separate actual prosthetic template based on said 3D virtual model of the paired prosthetic template;
   forming osteotomies in the patient's jawbone using the actual surgical template, securing implants in said osteotomies, and forming connection holes in the denture through the guide holes in the actual prosthetic template conforming to the connection holes in the 3D virtual model of the denture; and
   securing the denture to the implants by inserting attachment elements into the connection holes of the denture.

2. The method of claim 1 in which the securing step comprises inserting connecting elements in the form of implant abutment cylinders in the connection holes in the denture.

3. The method of claim 2 in which the step or forming the connection holes in the denture comprises making the connection holes larger than the cylinders to thereby leave space between the connection holes and the cylinders, and the securing step comprises introducing uncured resin in the space and curing the introduced resin to help secure the abutment cylinders to the denture.

4. The method of claim 3 in which the securing step comprises securing the implant abutment cylinders and denture to the implants with abutment screws.

5. The method of claim 4 in which the implant cylinders include axial channels through which the abutment screws pass, and including the step of filling the access channels with a retrievable, tooth-colored or pink material.

6. The method of claim 1 in which the forming of connection holes in the denture comprises mating the denture with the paired prosthetic template and drilling the connection holes in the denture through the guide holes in the paired prosthetic template while mated with the denture.

7. The method of claim 1 in which the processing comprises using a computer platform programmed with computer-aided design software to generate the virtual model.

8. The method of claim 7 in which the step of using a computer platform comprises interactively adjusting the virtual model through inputs via an interface with the platform.

9. The method of claim 1 in which the step of fabricating the prosthetic template comprises using a computer platform programmed with computer-aided manufacturing software.

10. The method of claim 1 in which the fabricating of the paired prosthetic template further comprises lining the guide holes therein with hard material inserts to reduce erosion and error due to rotation of dental drills in the guide holes.

11. The method of claim 1, wherein the step of providing a denture comprises providing a denture with replacement teeth.

12. The method of claim 11, wherein the step of forming connection holes in the denture comprise forming the guide holes and the connection holes to conform in location and orientation to the implants and to clear the replacement teeth.

13. The method of claim 1, wherein the step of fabricating the templates and forming the connection holes in the denture comprise axially lining up the guide holes in each of the templates with the connection holes in the denture and with the implants.

14. The method of claim 1, wherein the step of fabricating the prosthetic implant comprises forming the guide holes therein for passage through them of attachment elements for connecting the denture to the implants when the implants are in place in the patient's mouth, the denture in in place over the implants, and the prosthetic implant is over the denture.

15. The method of claim 1, wherein the step of forming connection holes through the denture comprises forming the connection holes so that they line up axially with the implant osteotomies.

16. The method of claim 1, further including the step of placing the implants in the patient's jawbone in the osteotomies created in the step of forming osteotomies.

17. The method of claim 1, wherein the step of forming connection holes in denture comprises making the connection holes larger than the attachment elements to leave free space for fine adjustment of the denture relative to the implants.

18. The method of claim 1, wherein the step of fabricating the prosthetic template comprises lining the guide holes in the prosthetic template with material protecting the prosthetic template from damage due to rotation of dental instrumentation therein.

19. The method of claim 1, further including placing abutment cylinders loosely fitting in the connection holes of the denture to thereby leave space around the cylinders allowing fine adjustment of the denture relative to the implants, and filling the space with curable resin and curing the resin to secure the denture in place following fine adjustment.

* * * * *